United States Patent [19]

Woodgrift et al.

[11] Patent Number: 5,149,326
[45] Date of Patent: Sep. 22, 1992

[54] ADJUSTABLE CATHETER CONTAMINATION SHIELD

[75] Inventors: Randal W. Woodgrift, Laguna Niguel; Gregory P. Welsh, Newport Beach, both of Calif.

[73] Assignee: Baxter International Inc., Deerfield, Ill.

[21] Appl. No.: 826,280

[22] Filed: Jan. 17, 1992

Related U.S. Application Data

[63] Continuation of Ser. No. 586,626, Sep. 21, 1990, abandoned.

[51] Int. Cl.⁵ .............................................. A61M 25/00
[52] U.S. Cl. ..................................... 604/163; 604/171
[58] Field of Search ......................... 604/163, 171, 172

[56] References Cited

U.S. PATENT DOCUMENTS

| | | |
|---|---|---|
| 2,937,643 | 5/1960 | Elliot . |
| 3,185,151 | 5/1965 | Czorny . |
| 3,335,723 | 8/1967 | Waldman, Jr. .................. 604/163 |
| 3,463,152 | 8/1969 | Sorenson . |
| 3,709,223 | 1/1973 | Macalalad et al. ............... 604/163 |
| 3,825,001 | 7/1974 | Bennet et al. .................... 604/163 |
| 3,894,540 | 7/1975 | Bonner, Jr. . |
| 4,051,849 | 10/1977 | Poncy . |
| 4,160,450 | 7/1979 | Doherty . |
| 4,327,723 | 5/1982 | Frankhouser . |
| 4,333,455 | 6/1982 | Bodicky . |
| 4,473,067 | 9/1984 | Schiff . |
| 4,515,592 | 5/1985 | Frankhouser .................... 604/163 |
| 4,551,137 | 11/1985 | Osborne ........................... 604/171 |
| 4,568,334 | 2/1986 | Lynn . |
| 4,613,329 | 9/1986 | Bodicky ........................... 604/163 |
| 4,634,433 | 1/1987 | Osborne ........................... 604/163 |
| 4,637,404 | 1/1987 | Gessman . |
| 4,767,409 | 8/1983 | Brooks ............................. 604/163 |
| 4,834,710 | 5/1989 | Fleck ............................... 604/163 |
| 4,836,199 | 6/1989 | Palmer ............................. 604/163 |
| 4,840,613 | 6/1989 | Balbierz ........................... 604/163 |

FOREIGN PATENT DOCUMENTS

| | | |
|---|---|---|
| 0311427 | 10/1988 | European Pat. Off. . |
| 1566588 | 2/1971 | Fed. Rep. of Germany . |
| 1566773 | 2/1971 | Fed. Rep. of Germany . |
| 1791236 | 4/1971 | Fed. Rep. of Germany . |
| 5906785 | 8/1980 | Fed. Rep. of Germany . |
| 2120413 | 8/1972 | France . |
| 2164738 | 8/1973 | France . |
| 1240312 | 7/1971 | United Kingdom . |
| 1446450 | 8/1976 | United Kingdom . |
| 1493257 | 11/1977 | United Kingdom . |
| 2007507 | 5/1979 | United Kingdom . |
| 1590796 | 6/1981 | United Kingdom . |

*Primary Examiner*—Paul J. Hirsch
*Attorney, Agent, or Firm*—Walter A. Hackler; Kurt A. MacLean

[57] ABSTRACT

An adjustable catheter contamination shield includes a distal fitting, a proximal fitting and a collapsible shield, disposed between said distal and proximal fittings, for enclosing an adjustable space therebetween and for preventing contact with a portion of the catheter disposed between the distal and proximal fittings. The shield is supported in a collapsed configuration and controlled expansion thereof is provided when the distal and proximal fittings are moved apart from one another, the controlled expansion enabling visual observation through an expanded portion of the collapsible shield when the distal and proximal fittings are moved apart from one another.

59 Claims, 5 Drawing Sheets

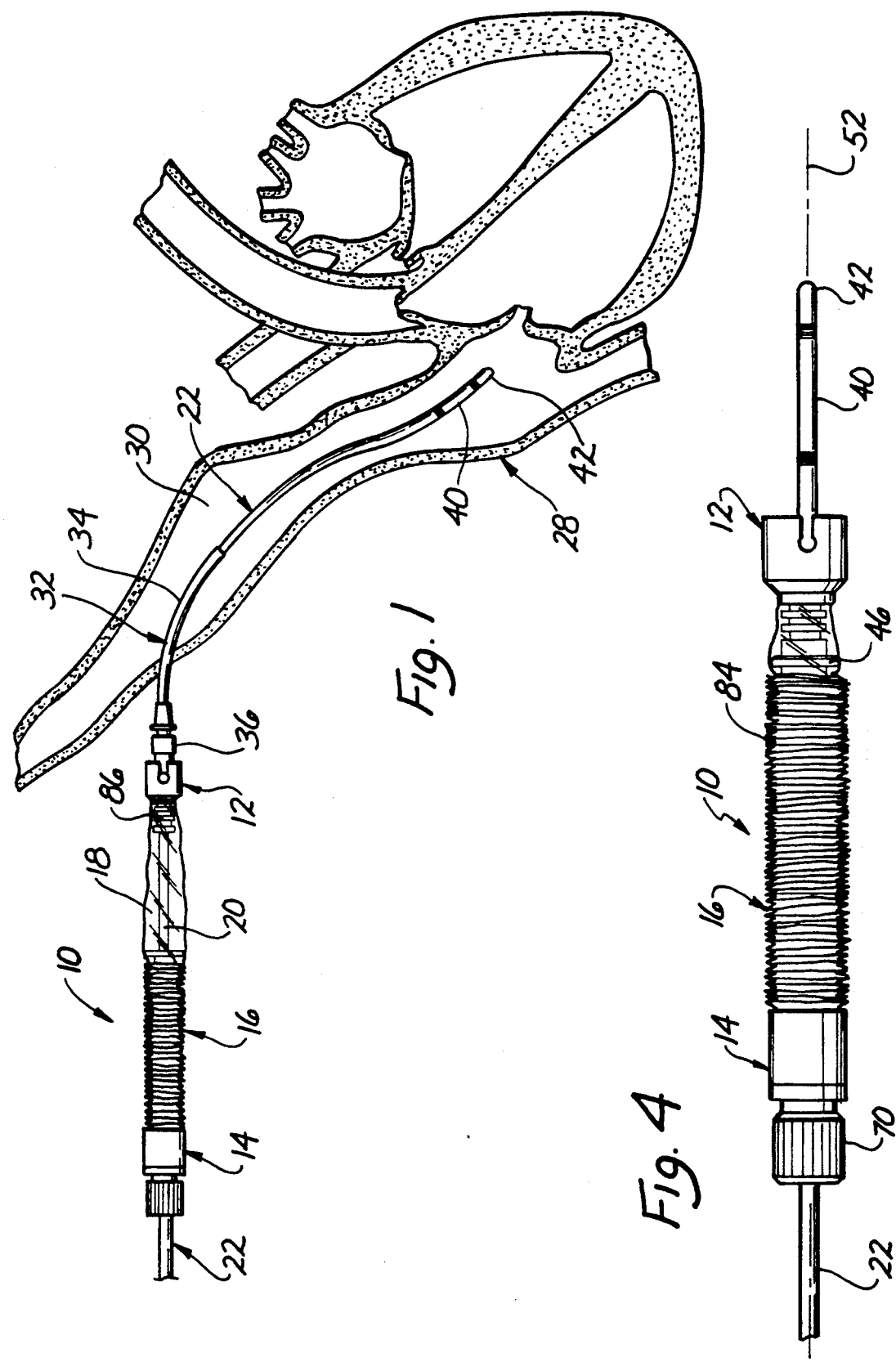

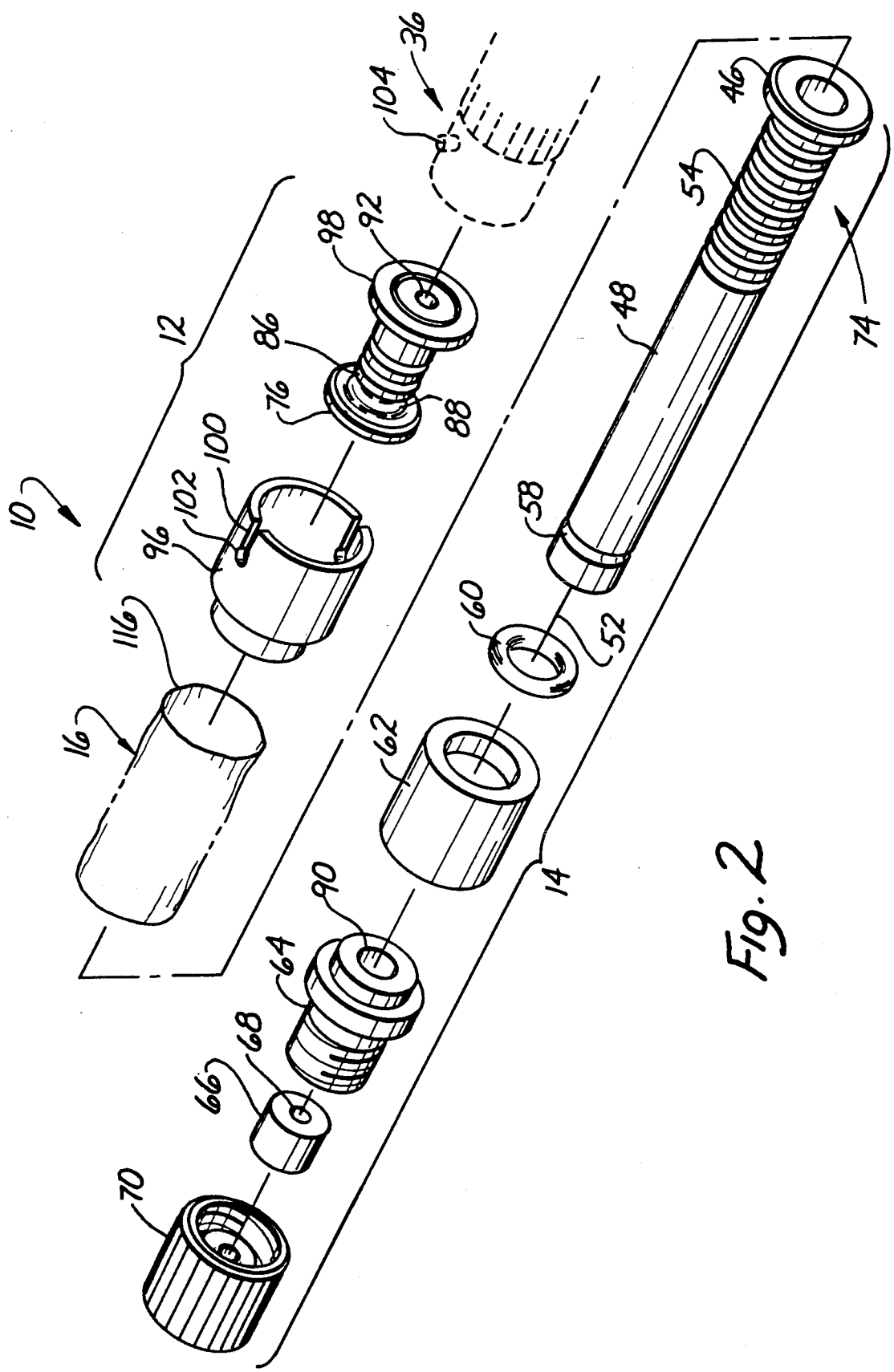

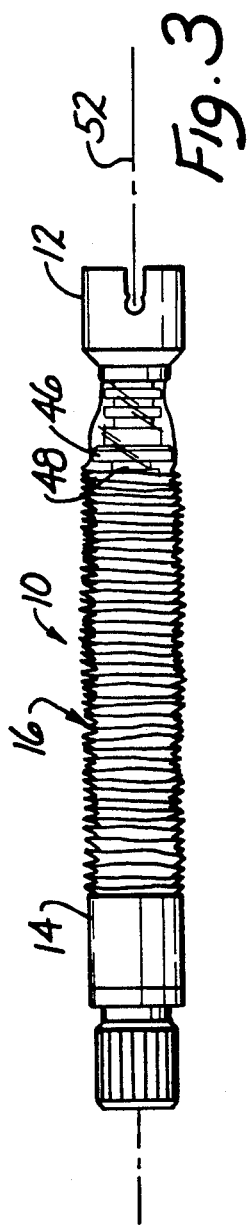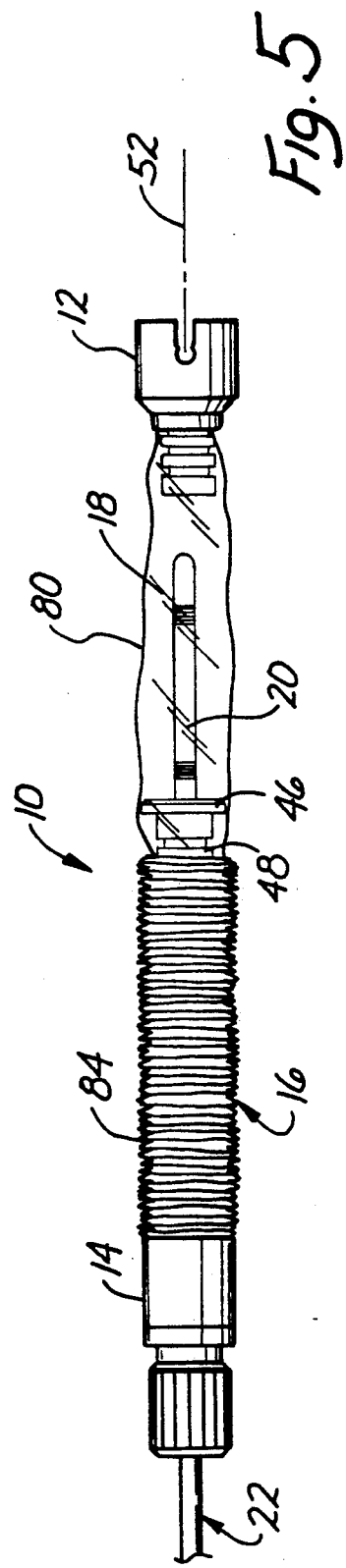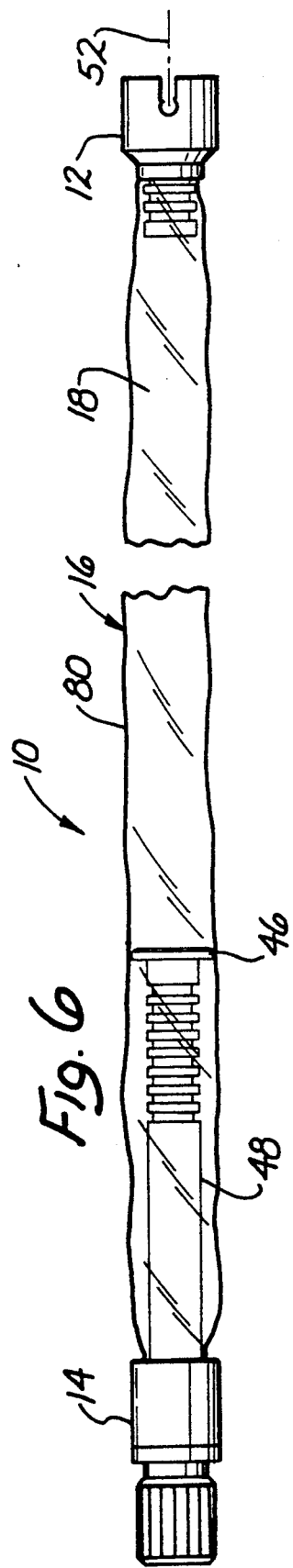

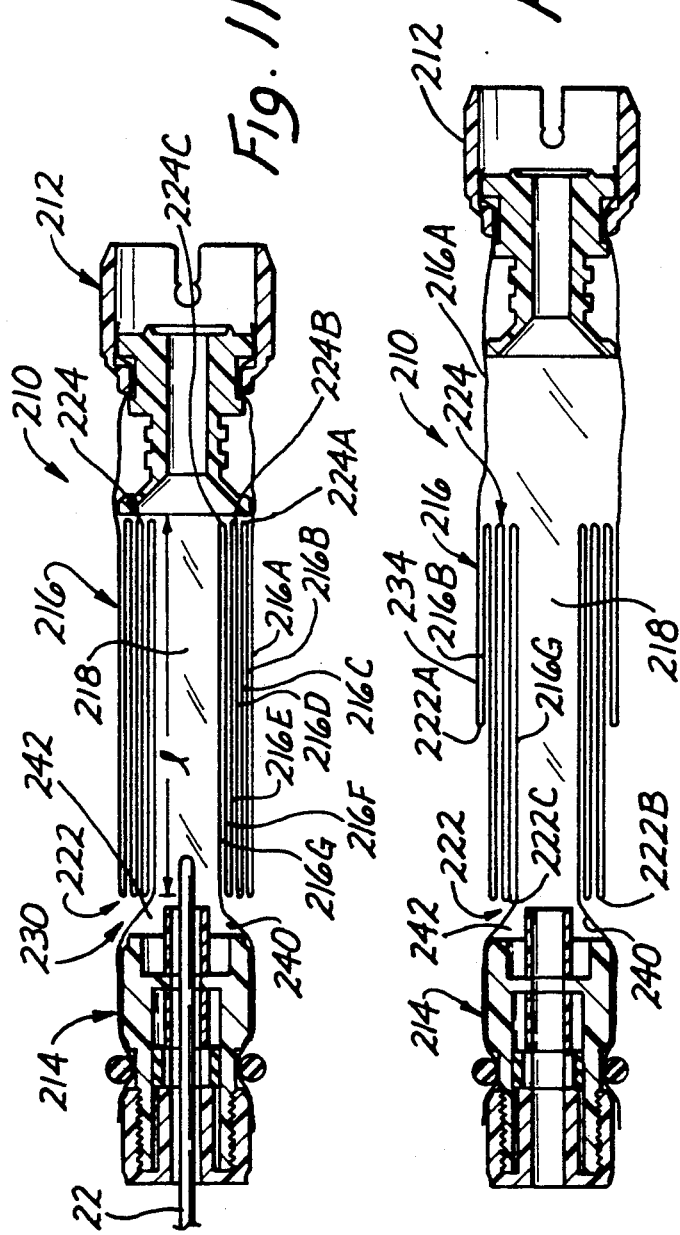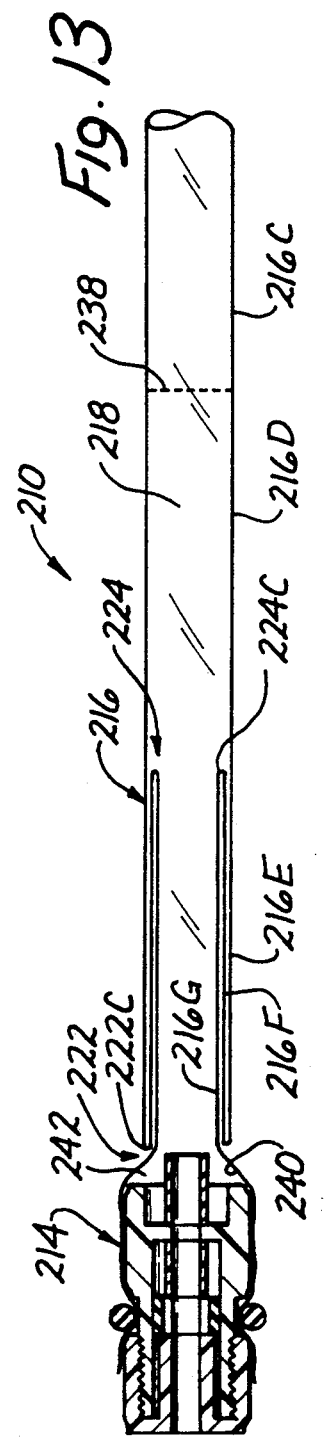

ADJUSTABLE CATHETER CONTAMINATION SHIELD

This is a continuation of application Ser. No. 07/586,626 filed on Sep. 21, 1990 now abandoned.

The present invention generally relates to apparatus for preventing the contamination of a catheter, or the like, as it is inserted into and withdrawn from a body cavity or vessel. More particularly, the present invention is directed to apparatus including an expandable shield for providing a contamination free environment for a catheter, or the like. The present invention is useful with any number of elongate tools for insertion into a body for measuring body functions. Such tools include, but are not limited to, pacing probes, intracranial catheters, urethral catheters, and fiber-optic catheters and the like.

In view of commonly accepted procedures for the utilization of such catheters within a venous vessel, such as, for example, balloon-tipped catheters, which include the adjustment of catheter depth, or inserted length, it is most desirable to provide a barrier to contamination of the exposed catheter portion exterior to the body.

A number of prior art devices have addressed this problem and utilized a protective shield such as a thin, plastic, flexible and collapsible hollow sleeve, which is disposed exterior to the catheter and supported between distal and proximal fittings. For example, see U.S. Pat. Nos. 4,327,723 and 4,515,592.

In accordance with the teachings of the hereinabove referenced patents, a catheter may be inserted through proximal and distal fittings and a collapsed sleeve before insertion into a venous vessel or the like. The collapsed sleeve may have a length of up to ten centimeters, in view of the fact that it is desirable for the sleeve to be expanded to lengths as long as one meter for providing a contamination free environment for the catheter.

To facilitate the insertion of the catheter through the collapsed sleeve, prior devices have provided a length of tube, approximately equal to the length of collapsed sleeve, which is disposed between proximal and distal fittings in order to provide a passage through the collapsed sleeve and prevent rupture, or puncture, of the collapsed sleeve during insertion of the catheter therethrough. (U.S. Pat. Nos. 4,327,723 and 4,515,592) Once the distal and proximal fittings of the prior art device are pulled apart and disconnected from the interconnecting tube, the sleeve is expanded and reinsertion of the catheter therethrough is difficult, if not impossible, due to difficulty in alignment of the proximal and distal ends with one another.

This is due to the fact that the prior art sleeves do not expand in a controlled manner in which the sleeve is divided into a totally collapsed portion and a totally expanded portion, the latter enabling visual observation of the catheter therethrough. Rather, in prior art devices the expansion of the sleeve is uncontrolled which results in all of the sleeve being partially expanded between the distal and proximal fittings thus obscuring visual observation of the catheter therethrough.

The present invention provides a means for controlling the expansion of a contamination shield as the distal and proximal fitting are pulled apart from one another. This enables the alignment of the proximal and distal ends without separate interconnection thereof by a tube or the like. Further, one embodiment of the present invention enables tension to be applied to expanded portions of the shield, thus insuring visual observation of the catheter therethrough for facilitating alignment of the distal and proximal fittings in order to thread the catheter through the shield.

SUMMARY OF THE INVENTION

An adjustable catheter contamination shield in accordance with the present invention generally includes a distal fitting having a bushing for coupling to an introducer and means, defining a bore through the distal fitting, for enabling the passage of the catheter therethrough. A proximal fitting is provided which also includes means, defining a bore therethrough, for enabling passage of the catheter.

A collapsible shield is disposed between the distal and the proximal fittings which provides means for enclosing an adjustable space therebetween and preventing contact with a portion of the catheter disposed between the distal and the proximal fittings.

Means are provided for controlling expansion of the collapsible shield as the distal and proximal fittings are moved apart form one another in order that a portion of the collapsible shield remains in a totally collapsed configuration until of the collapsible shield is in an expanded configuration.

This is to be distinguished for prior art devices which offer no control of the expansion of a collapsible sleeve or shield. That is, in prior art devices, when the distal and proximal fittings are pulled apart in order to expand the shield therebetween, the sleeve is free to expand over its entire length.

Importantly, the controlled expansion feature of the present invention enables visual observation of the catheter through a fully expanded portion of the catheter shield means despite the amount of expansion of the catheter shield means. In accordance with the present invention the controlled expansion causes the unexpanded portion of the catheter shield means to remain in a fully, or near fully collapsed configuration as the catheter shield expands when the distal and proximal fittings are moved apart from one another.

More specifically, the means for controlling expansion of the collapsible shield includes means defining a plurality of folds in said collapsible shield for enabling portions of said collapsible shield to be disposed in generally parallel relationship with one another when said collapsible shield is in a collapsed configuration. In addition the means defining a plurality of folds is operable for enabling said portions of said collapsible shield to be disposed in a generally serial relationship with one another when said collapsible shield is in an expanded configuration. This provides a convoluted structure in which portions of the collapsible shield overlay one another.

Alternatively, separate means may be provided for supporting the shield means in a collapsed configuration and, importantly, for causing controlled expansion of the collapsed shield means along a longitudinal axis thereof from a selected number of points along the collapsed configuration. Preferably, in this embodiment, the collapsible shield expands from one end of the collapsed configuration when the distal and the proximal fittings are moved apart from one another.

More particularly, the means for supporting the shield means may be disposed proximate the proximal fitting and interconnected therewith. The means for supporting the shield may comprise a flange having an outside diameter sufficient to prevent passage of the shield means thereover without movement of the distal and proximal fittings from one another.

Further, the shield means may be formed from a material enabling visual observation of the catheter through an expanded portion thereof when the expanded portion is in a state of tension. In conjunction therewith, the flange, as hereinabove recited, provides a means for causing the expanded portion of the shield to be in a state of tension which enables the visual observation of the catheter therethrough, when the distal and proximal fittings are moved apart from one another.

To prevent strain on the catheter passing through the proximal and distal fittings, one or both of the fittings may include a flexible member, or tube, for preventing forces to be applied to the catheter due to manipulation of the proximal and distal fittings and the catheter during insertion and withdrawal of the latter from a vas, or due to patient movement.

BRIEF DESCRIPTION OF THE DRAWINGS

A better understanding of the present invention may be had by consideration of the following detailed description, taken in conjunction with the accompanying drawings, in which:

FIG. 1 is a side view of one embodiment of an adjustable catheter contamination shield in accordance with the present invention depicting its use with an introducer for inserting a catheter into a heart;

FIG. 2 is an exploded perspective representation of the contamination shield shown in FIG. 1;

FIG. 3 is a side view of the shield of the present invention, shown in fully collapsed condition;

FIG. 4 is a side view of the shield shown in FIG. 3 with the catheter inserted therethrough;

FIG. 5 is a side view of the shield shown in FIG. 3 with a portion of the shield shown in an extended state with the catheter visible therethrough;

FIG. 6 is a side view of the shield shown in FIG. 3 in a totally expanded condition.

FIG. 11 is a cross-sectional view of an alternative embodiment of the present invention in which the collapsible shield includes a plurality of folds which enable portions thereof to be disposed in a generally parallel relationship when the collapsible shield is in a collapsed configuration; and FIG. 12 and 13 are a cross-sectional views of the embodiment shown in FIG. 11 illustrating the collapsible shield in various states of expansion in which the portions thereof are in a serial relationship;

DETAILED DESCRIPTION OF THE DRAWINGS

Figure 7:
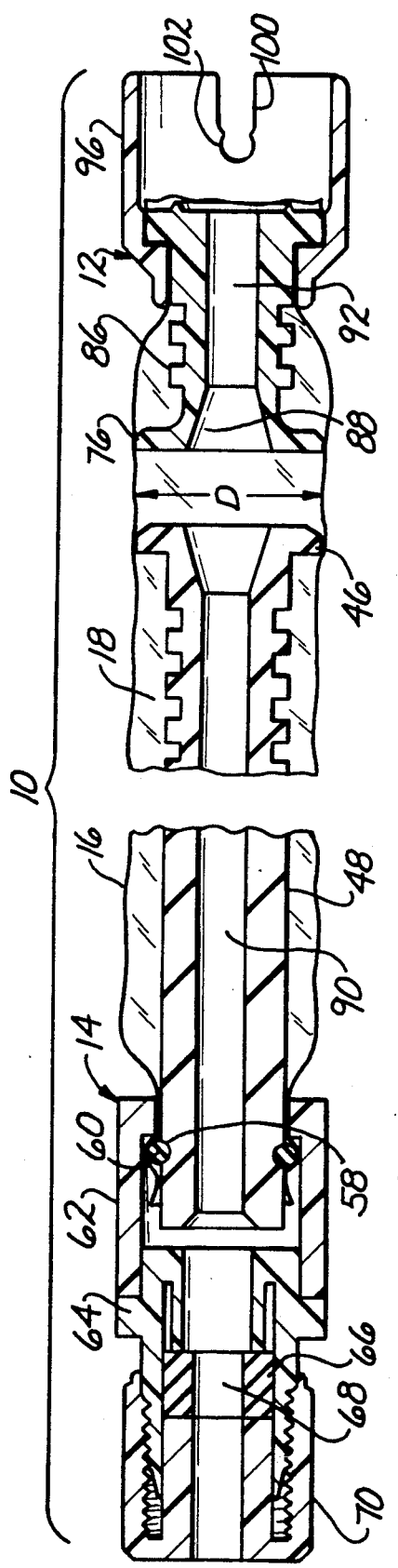
FIG. 7 is a cross-sectional view of a portion of a proximal fitting in accordance with the present invention.

Turning now to FIGS. 1-6, there is shown an adjustable catheter contamination shield 10 in accordance with the present invention generally including a distal fitting 12, a proximal fitting 14, and a collapsible shield 16, disposed between the distal and proximal fittings 12, 14 which provides means for enclosing an adjustable space 18 therebetween and for preventing contact with a portion 20 of a catheter 22 disposed between the distal and proximal fittings 12, 14. (See FIGS. 1, 5 and 6) As diagrammatically shown in FIG. 1, the catheter contamination shield is positioned for the insertion of the catheter 22 into a heart 28 through an internal jugular vein 30 by means of an introducer 32 which includes an introducer sheath 34 and a fitting 36, the introducer 32, including the sheath 34 and fitting 36 being of conventional design. As shown, the catheter 22 may include a balloon portion 40 disposed proximate a tip 42, the balloon portion being commonly used and well-known in the art. It should be appreciated that although a balloon type catheter is shown herein, the catheter contamination shield 10 is suitable for use with a great number of catheter types.

FIG. 2 is an exploded perspective view of the catheter contamination shield 10 showing in greater detail the distal fitting 12 and the proximal fitting 14. A flange 46 formed as an integral portion of a tube 48 provides a means for supporting the shield 16 in the collapsed configuration and, in addition, causing the collapsed shield to expand along a longitudinal axis 52 as shown in FIGS. 3, 5 and 6 and hereinafter described in greater detail.

It should be appreciated that, while the flange 46 and tube 48 are shown proximate and connected to the proximal fitting 14, alternatively the flange 46 with tube 48 may be connected with the distal fitting 12, such alternative arrangement not being shown in the drawings.

The tube 48, which may be formed from any suitable flexible material, provides a passage through the collapsed shield 16 for the catheter 22. In addition, a ribbed portion 54 proximate the flange 46, provides a means for reducing strain on the catheter passing through the tube 48 which may occur through manual manipulation of the catheter contamination shield 10 and catheter 22 as the latter is advanced through a venous vessel such as the jugular vein 30 as shown in FIG. 1. This feature of the present invention will be discussed hereinafter in greater detail.

A groove 58 disposed in the flexible tube 48 along with an O-ring 60 and a sleeve 62 provides means for fixing the collapsible shield 16 to the proximal fitting 14 as more clearly shown in cross-section in FIG. 7.

Coupled to the sleeve 62 is a threaded fitting 64 enclosing a gland 66, having an orifice 68 therethrough sized for fitting into the catheter 22 and held in position by a cap 70 adapted for threaded engagement with the fitting 64 with the bushing 66 there-enclosed.

As best shown in FIGS. 5, 6 and 7, the flange 46 has an outside diameter D which is sufficient to prevent the passage of the shield 16 therepast without movement of the distal and proximal fittings 12, 14 from one another. Depending upon the material of construction of the shield 16, this function of the flange 46 in both enabling selected expansion of the shield therepast and for supporting the shield in a collapsed configuration may be obtained when the flange diameter D is greater than the inside diameter of the shield 16.

It should be appreciated that while the flange is shown disposed at an end 74, it may be disposed at any intermediate position or a number of similar flanges, not shown, may be disposed along the tube 48 for controlling the expansion of the shield 16 therepast. The tube 48 provides a passage through the collapsed shield 16 and additionally when the shield 16 is collapsed over the tube 48, the flange 46 is coaxially aligned with a flexible distal tube 76 thereby facilitating passage of the catheter 22 therethrough.

The shield 16 may be formed of a polyethylene type material or any other material facilitating the collapse thereof over the tube 48 and also, importantly, enabling the visual observation of the catheter 22 through an expanded portion 80 thereof as shown in FIG. 5 and 6.

The flange 46 hereinabove described in conjunction with providing a means for maintaining the shield in a collapsed configuration also performs the function of providing tension in an expanded portion 80 between the flange 46 and the distal fitting 12 to enable visual observation of the catheter 22 disposed therein. This state of tension is sufficient to remove a pleating 84 of the shield 16 for enabling the hereinabove referenced visual observation of the catheter.

This feature is important in that once the distal and proximal fittings 12, 14 are moved to a spaced apart relationship, the catheter 22 can still be "threaded" or passed from the proximal fitting 14 through the distal fitting 12 by visual alignment thereof through the taut portion 80 of the shield 16. Hence, the structure of the present invention enables the function of threading the catheter 22 through spaced apart proximal and distal fittings 12, 14 which results in a shield providing far greater capability with regard to movement and withdrawal of a catheter than was heretofore possible.

Turning again to FIGS. 1 and 2, the distal fitting 12 may include a distal tube 76, formed of a flexible material similar to that utilized in the tube 48 and also may include a a plurality of spaced apart ribs 86 which provides a means for preventing strain on the catheter 22 during manipulation thereof as hereinabove discussed in connection with the proximal tube 48 and the ribbed portion thereof 54.

The threaded fitting 64 and the distal tube 76 include bores 90, 92 for enabling passage of the catheter 22 therethrough. In addition, the distal fitting 12 includes a bushing 96 sized for passing over the tube 76 and sealably engaging a flange 98 disposed on the tube 76 to the introducer 32 by way of the introducer fitting 36. The bushing 96 may include a slot 100 and detent 102 for engaging a prong 104 on the introducer fitting 36 in a conventional manner.

Figure 10:
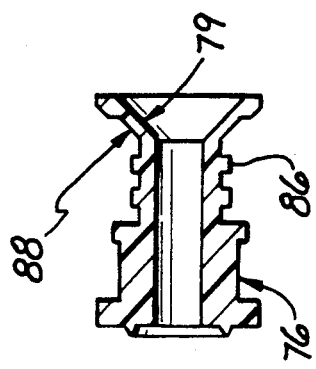
FIG. 10 is a cross-sectional view of the fitting shown in FIG. 8.
Figure 8:
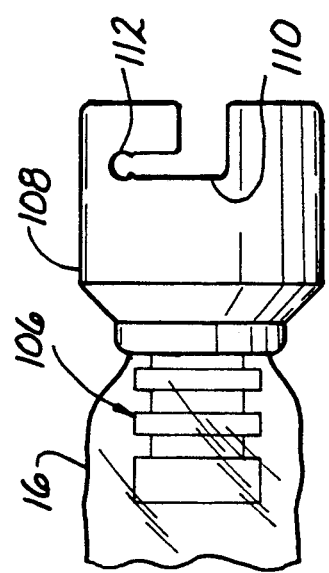
FIG. 8 is a side view of an alternative bushing in accordance with the present invention.

Alternatively, as shown in FIG. 10, an alternative bushing 108 may include a bayonet-type slot 110 with detent 112 for engaging the prong 104 in a conventional manner. In addition, a distal tube 106 may be utilized which does not include a flange thereon depending on the degree of strain relief desired for the catheter 22 as hereinafter discussed.

Figure 9:
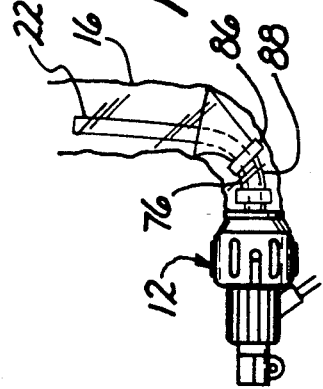
FIG. 9 is a side view of a fitting in accordance with the present invention which includes a tubular portion having a plurality of spaced apart ribs thereon for enabling up to a 90° turn thereof, as shown, without kinking of a catheter therein.

As shown in FIGS. 9 and 10, the ribs 86 and a thin wall body portion 88 enable the distal fitting 12 to be turned, or bent, up to approximately 90° without kinking of the catheter therein.

The distal tube 76 may include a flange 78 similar to flange 46 on the proximal fitting 14, which may include a 45° inside angle 79 for enabling the catheter 22 to turn therein. The distal tube 76 may be formed from any soft, pliable material having, for example, a 35 hardness durometer.

The ribs 86 provide support and allow strain relief so the catheter may move freely at angles less than about 90° without causing internal buckling, or kinking, of the catheter 22. In fact, tests have shown that catheter turns of up to 135° can be achieved in some instances without damage to the catheter. This of course is dependent on the type of catheter used.

It should be appreciated that because the distal fitting 12 is locked onto the introducer 32, which is rigidly sutured to a patient, not shown, when the catheter 22 is manipulated in the general course of its use, or patient movement occurs, a catheter kink may be caused. Such kinking is prevented by the structure of the present invention. Kinking of this nature typically causes internal damage to the catheter lumens, not shown, which can seriously impair the usefulness thereof. In the case of fiber-optic catheters, fiber kink damage results in light transmission diminishment which decreases the transfer of information therethrough.

A distal end 116 of the shield 16 may be fixed to the distal fitting 12, for a compressed fit between the flange 98 and the bushing 96.

Turning now to FIG. 11, there is shown an alternative embodiment 210 in accordance with the present invention generally including a distal fitting 212, a proximal fitting 214, and a collapsible shield 216, disposed between the distal and proximal fittings 212, 214 which provides means for enclosing an adjustable space 218 therebetween and for preventing contact with the catheter 22, not shown in FIG. 11, as hereinabove described. The distal fitting may be identical to the distal fitting 12 hereinabove described and the proximal fitting 214 is similar to the proximal fitting 14 without the tube 48 and flange 46.

The collapsible shield 216 includes a plurality of folds 222, 224, which provide means for both enabling portions 216A-G of the collapsible shield 216 to be disposed in generally parallel relationship with one another when the collapsible shield 216 is in a collapsed configuration as shown in FIG. 12, and for enabling the portions 216A-G of the collapsible shield to be disposed in a generally serial relationship with one another when said collapsible shield is in an expanded configuration as shown in FIGS. 12 and 13.

As shown in FIGS. 11, 12 and 13, the folds may be disposed on each end 230, 232 of the collapsible shield portions 216A-G with each of the collapsible shield portions 216A-G having approximately equal length, l.

In this manner the portions 216A-G overlay one another to provide a compact, or collapsed shield 216 configuration as shown in FIG. 11. The folds 222, 224 define a convoluted structure for the collapsible shield 216 which provides means for controlling the expansion of the collapsible shield 216 as the proximal and distal fittings 212, 214 are moved apart from one another as shown in FIGS. 12 and 13.

As illustrated in FIG. 12 when the distal end 212 is pulled away from the proximal fitting 214 the topmost fold 222A moves along a next outside layer 234 of the collapsible shield 216. Underlying folds 222B-C and 224A-C do not move due to lack of sufficient friction between portions 216A-B. As indicated in FIGS. 12 and 13, the portions 216A-B are arranged in a serial configuration after the distal and proximal fittings have been moved apart from one another, only portions 216C and 216D being shown along with a crease 238 (dashed line) indicating the position of the original fold 222B.

The embodiment 210 of the present invention features structure in which the collapsible shield portions 216A-G are generally tubular and smooth between the folds 222, 224 on each end thereof. Because the collapsible shield portions 216A-G are not "bunched", or compacted as in the hereinabove described collapsible shield 16, the expanded configuration as shown in FIG. 13 will have greater visibility therethrough without the necessity of providing tension between the distal and proximal fittings 212, 214.

It is important in the embodiment 210 that the inside portion 216G of the collapsible shield 216 is directly connected to the proximal fitting 214 by a smooth section 240 in order that the catheter 22 can be passed into the space 218 without catching, or snagging, of the folds 222. Because of the continuous nature of an entrance 242 to the area 218, unrestricted passage of the catheter into the collapsible shield 216 in provided.

A procedure in accordance with the present invention, and utilizing the structure thereof, provides a contamination free environment exterior to a body, such as a heart 28, for the catheter 22 which includes steps of coupling the distal fitting 12 of the contamination shield 10 to an introducer 32, the introducer being adapted for insertion into a venous vessel such as the jugular vein 30 as hereinbefore described.

Thereafter, the procedure in accordance with the present invention includes passing catheter 22 through the proximal fitting 14 and into the contamination free area 18 enclosed by the expandable shield 16 disposed between the distal and proximal fittings 12 and 14.

The shield 16 is then expanded from the flange 46 to enable visual observation of the catheter portion 20 passing between the distal and proximal fittings 12, 14.

In addition the catheter may be manipulated while it is within the expandable shield and the manipulation including bending of the catheter within the proximal and/or distal fitting up to angles of approximately 90° without kinking thereof.

Although there has been hereinabove described specific arrangements of a catheter contamination shield and procedure in accordance with the present invention for the purpose of illustrating the manner in which the invention can be used to advantage, it will be appreciated that the invention is not limited thereto. Accordingly, any and all modifications, variations, or equivalent arrangements, which occur to those skilled in the art, should be considered to be within the scope of the invention as defined in the appended claims.

What is claimed is:

1. An adjustable catheter contamination shield comprising:
   a distal fitting including bushing means for coupling to an introducer and means, defining a bore through the distal fitting, for enabling passage of a catheter therethrough;
   a proximal fitting including means, defining a bore therethrough, for enabling passage of a catheter through the proximal fitting;
   collapsible shield means, disposed between said distal and proximal fitting, for enclosing an adjustable space therebetween and for shielding a portion of a catheter disposed between the distal and proximal fittings; and
   means for supporting the shield means in a collapsed configuration and for causing the collapsed shield means to expand along a longitudinal axis thereof from only one portion of the collapsed configuration at a time when the distal and proximal fittings are moved apart from one another.

2. The adjustable catheter contamination shield according to claim 1 wherein said means for supporting the shield means is disposed proximate said proximal fitting.

3. The adjustable catheter contamination shield according to claim 2 wherein said means for supporting the shield means is interconnected with said proximal fitting.

4. The adjustable catheter contamination shield according to claim 3 wherein said means for supporting the shield means is disposed within said shield means.

5. The adjustable catheter contamination shield according to claim 4 wherein said means for supporting the shield means comprises a flange having an outside diameter sufficient to prevent passage of the shield means thereover without movement of the distal and proximal fittings from one another.

6. The adjustable catheter contamination shield according to claim 5 wherein the means for supporting the shield means further comprises a flexible tube means, disposed between said flange and proximal fitting and coaxially aligned therewith, for providing a passage through the collapsed shield means and for reducing strain on a catheter passing therethrough.

7. The adjustable catheter contamination shield according to claim 67 wherein aid distal fitting includes flexible tube means coaxially aligned therewith for reducing strain on a catheter passing therethrough.

8. The adjustable catheter contamination shield according to claim 7 wherein the distal fitting flexible tube means includes means defining a plurality of spaced apart ribs thereon, for enabling the distal fitting flexible tube means to be bent up to approximately 90° without kinking of a catheter disposed therein.

9. The adjustable catheter contamination shield of claim 1 wherein the means for causing the collapsed shield means to expand causes the collapsed shield means to expand along a longitudinal axis thereof from only one end of the collapsed configuration at a time.

10. The adjustable catheter contamination shield of claim 9 wherein the means for causing the collapsed shield means to expand is positioned between the distal and proximal fittings and wherein the means for causing the collapsed shield means to expand causes the collapsed shield means to expand only in a direction toward the distal fitting.

11. The adjustable catheter contamination shield of claim 10 wherein the means for causing the collapsed shield means to expand causes portions of the collapsed configuration closest to the distal fitting to expand before more proximal collapsed shield portions.

12. The adjustable catheter contamination shield of claim 1 wherein the shield means prevents contact with a portion of a catheter disposed between the distal and proximal fittings.

13. An adjustable catheter contamination shield comprising:
   a distal fitting including bushing means for coupling to an introducer and means, defining a bore through the distal fitting, enabling passage of a catheter therethrough;
   a proximal fitting including means, defining a bore therethrough, for enabling passage of the catheter through the proximal fitting;
   collapsible shield means, disposed between said distal and proximal fittings, for enclosing an adjustable space therebetween and for preventing contact with a portion of the catheter disposed between the distal and proximal fittings, the shield means being formed of a material enabling visual observation of the catheter through an expanded portion of the shield means, when the catheter is disposed between the distal and proximal fittings; and means for supporting the shield means in a collapsed configuration and for producing the expanded portion, through which the catheter is observed, while maintaining a remainder of the shield means in the collapsed configuration, as the distal and proximal fittings are moved apart from one another.

14. The adjustable catheter contamination shield according to claim 13 wherein said means for supporting the shield means is disposed proximate said proximal fitting.

15. The adjustable catheter contamination shield according to claim 14 when said means for supporting the shield means is attached with said proximal fitting.

16. The adjustable catheter contamination shield according to claim 15 wherein said means for supporting the shield means is disposed within said shield means.

17. The adjustable catheter contamination shield according to claim 16 wherein said means for supporting the shield means comprises a flange having an outside diameter sufficient to prevent passage of the shield means thereover without movement of the distal and proximal fittings from one another.

18. The adjustable catheter contamination shield according to claim 17 wherein the means for supporting the shield means further comprises a flexible tube means, disposed between said flange and proximal fitting and coaxially aligned therewith, for providing a passage through the collapsed shield means and for reducing strain on a catheter passing therethrough.

19. The adjustable catheter contamination shield according to claim 18 wherein said distal fitting includes flexible tube means coaxially aligned therewith for reducing strain on a catheter passing therethrough.

20. An adjustable catheter contamination shield comprising:
- a distal fitting including bushing means for coupling to an introducer and means, defining a bore through the distal fitting, for enabling passage of a catheter therethrough;
- a proximal fitting including means, defining a bore therethrough, for enabling passage of a catheter through the proximal fitting;
- collapsible shield means, disposed between said distal and proximal fittings, for enclosing an adjustable space therebetween and for shielding a portion of a catheter disposed between the distal and proximal fittings; and
- means for supporting the shield means in a collapsed configuration and for causing the collapsed shield means to expand only from at least one selected point along the collapsed configuration.

21. The adjustable catheter contamination shield according to claim 20 wherein said at least one selected point along the collapsed configuration is positioned between the distal and proximal fittings.

22. The adjustable catheter contamination shield according to claim 21 wherein the one selected point is disposed at an end of the collapsed configuration.

23. The adjustable catheter contamination shield according to claim 22 wherein said means for supporting the shield means is disposed proximate said proximal fitting.

24. The adjustable catheter contamination shield according to claim 23 wherein aid means for supporting the shield means is interconnected with said proximal fitting.

25. The adjustable catheter contamination shield according to claim 24 wherein said means for supporting the shield means is disposed within said shield means.

26. The adjustable catheter contamination shield according to claim 25 wherein said means for supporting the shield means comprises a flange having an outside diameter sufficient to prevent passage of the shield means thereover without movement of the distal and proximal fittings from one another.

27. The adjustable catheter contamination shield according to claim 26 wherein the means for supporting the shield means further comprises a flexible tube means, disposed between said flange and proximal fitting and coaxially aligned therewith, for providing a passage through the collapsed shield means and for reducing strain on a catheter passing therethrough.

28. The adjustable catheter contamination shield according to claim 27 wherein said distal fitting includes flexible tube means coaxially aligned therewith for reducing strain on a catheter passing therethrough.

29. An adjustable catheter contamination shield comprising:
- a distal fitting including bushing means for coupling with an introducer and means, defining a bore through the distal fitting, for enabling passage of a catheter therethrough;
- a proximal fitting including means, defining a bore therethrough, for enabling passage of the catheter through the proximal fitting;
- collapsible shield means, disposed between said distal and proximal fittings, for enclosing an adjustable space therebetween and for preventing contact with a portion of the catheter disposed between the distal and proximal fittings, the shield means being formed of a material enabling visual observation of the catheter through an expanded portion thereof when the catheter is disposed between the distal and proximal fittings and the expanded portion is in a state of tension; and
- means, connected with one of said distal and proximal fittings, for supporting the shield means in a collapsed configuration with said distal and proximal fittings adjacent to one another for enabling the catheter to be threaded through the bores of the distal and proximal fittings, for causing the collapsed shield means to expand along a longitudinal area thereof from one end of the collapsed configuration, when the distal and proximal fittings are moved apart from one another, and for causing the expanded portion of the shield to be in the state of tension enabling visual observation of the catheter therethrough.

30. The adjustable catheter contamination shield according to claim 29 wherein said means for supporting the shield means is disposed proximate said proximal fitting.

31. The adjustable catheter contamination shield according to claim 30 when said means for supporting the shield means is interconnected with said proximal fitting.

32. The adjustable catheter contamination shield according to claim 31 wherein said means for supporting the shield means is disposed within said shield means.

33. The adjustable catheter contamination shield according to claim 32 wherein said means for supporting the shield means comprises a flange having an outside diameter sufficient to prevent passage of the shield means thereover without movement of the distal and proximal fittings from one another.

34. The adjustable catheter contamination shield according to claim 33 wherein the means for supporting the shield means further comprises a flexible tube means, disposed between said flange and proximal fitting and coaxially aligned therewith, for providing a passage through the collapsed shield means and for reducing strain on a catheter passing therethrough.

35. The adjustable catheter contamination shield according to claim 34 wherein said distal fitting includes flexible tube means coaxially aligned therewith for reducing strain on a catheter passing therethrough.

36. The adjustable catheter contamination shield according to claim 35 wherein the distal fitting flexible tube means includes means defining a plurality of spaced apart ribs thereon, for enabling the distal fitting flexible tube means to be bent up to approximately 90° without kinking of a catheter disposed therein.

37. An adjustable catheter contamination shield comprising:
   a distal fitting including bushing means for coupling to an introducer and first flexible tube means, coaxially aligned with said distal fitting, for enabling passage of a catheter therethrough and preventing strain to said catheter;
   a proximal fitting including second flexible tube means, coaxially aligned with aid proximal fitting, for enabling passage of a catheter therethrough and preventing strain to said catheter and;
   collapsible shield means, disposed between said distal and proximal fitting, for enclosing an adjustable space therebetween and for shielding with a portion of the catheter disposed between the distal and proximal fittings, said collapsible shield means being disposed over said first and second flexible tube means.

38. The adjustable catheter contamination shield according to claim 37 wherein said first and second flexible tube means include means defining a plurality of spaced apart ribs thereon, for enabling the first and second flexible tube means to be bent up to approximately 90° without kinking of a catheter disposed therein.

39. The adjustable catheter contamination shield according to claim 38 wherein the second flexible tube means includes means for supporting the shield means in a collapsed configuration and for causing the collapsed shield means to expand along a longitudinal axis thereof from one end of the collapsed configuration when the distal and proximal fittings are moved apart from one another.

40. The adjustable catheter contamination shield according to claim 39 wherein said means for supporting the shield means is disposed proximate said proximal fitting.

41. The adjustable catheter contamination shield according to claim 40 when said means for supporting the shield means is interconnected with said proximal fitting.

42. The adjustable catheter contamination shield according to claim 39 wherein said means for supporting the shield means is disposed within said shield means.

43. The adjustable catheter contamination shield according to claim 42 wherein said means for supporting the shield means comprises a flange having an outside diameter sufficient to prevent passage of the shield means thereover without movement of the distal and proximal fittings from one another.

44. An adjustable catheter contamination shield comprising:
   a distal fitting including bushing means for coupling to an introducer and means, defining a bore through the distal fitting, for enabling passage of a catheter therethrough;
   a proximal fitting including means, defining a bore therethrough, for enabling passage of the catheter through the proximal fitting;
   collapsible shield means, disposed between said distal and proximal fittings, for enclosing an adjustable space therebetween and for shielding a portion of the catheter disposed between the distal and proximal fittings; and
   means for controlling expansion of the collapsible shield means as the distal and proximal fittings are moved apart from one another in order that a portion of the collapsible shield means remains in a totally collapsed configuration until all of the collapsible shield means is in an expanded configuration.

45. The adjustable catheter contamination shield means according to claim 44 wherein said means for controlling expansion of the collapsible shield means includes means, defining a plurality of folds in said collapsible shield means, for enabling portions of said collapsible shield means to be disposed in generally parallel relationship with one another when said collapsible shield means is in the collapsed configuration.

46. The adjustable catheter contamination shield according to claim 45 wherein said folds are disposed on ends of the collapsible shield means portions.

47. The adjustable catheter contamination shield according to claim 46 wherein each of said collapsible shield means portions have approximately equal length.

48. The adjustable catheter contamination shield according to claim 47 wherein the collapsible shield means portions are generally tubular and smooth between the folds on each end thereof.

49. An adjustable catheter contamination shield comprising:
   a distal fitting including bushing means for coupling to an introducer and means, defining a bore through the distal fitting, for enabling passage of a catheter therethrough;
   a proximal fitting including means, defining a longitudinal extending bore therethrough, for enabling passage of the catheter through the proximal fitting;
   collapsible shield means, disposed between said distal and proximal fittings, for enclosing an adjustable space therebetween and for shielding a portion of the catheter disposed between the distal and proximal fittings; and
   means, defining a plurality of folds in said collapsible shield means, for both enabling portions of said collapsible shield means to be disposed in generally parallel longitudinally extending relationship with one another when said collapsible shield means is in a collapsed configuration and for enabling said portions of said collapsible shield means to be disposed in a generally serial relationship with one another when said collapsible shield means is in an expanded configuration.

50. The adjustable catheter contamination shield according to claim 49 wherein the folds are disposed on ends of the collapsible shield means portions.

51. The adjustable catheter contamination shield according to claim 50 wherein each of said collapsible shield means portions have approximately equal length.

52. The adjustable catheter contamination shield according to claim 51 wherein the collapsible shield means portions are generally tubular and smooth between the folds on each end thereof.

53. An adjustable catheter contamination shield comprising:
- a distal fitting including bushing means for coupling to an introducer and first flexible tube means, coaxially aligned with aid distal fitting, for enabling passage of a catheter therethrough and preventing strain to said catheter;
- a proximal fitting including second flexible tube means, coaxially aligned with aid proximal fitting, for enabling passage of a catheter therethrough and preventing strain to said catheter;
- collapsible shield means, disposed between said distal and proximal fittings, for enclosing an adjustable space therebetween and for preventing contact with a portion of the catheter disposed between the distal and proximal fitting; and
- means, defining a plurality of folds in said collapsible shield means, for both enabling portions of said collapsible shield means to be disposed in generally parallel relationship with one another when said collapsible shield means is in a collapsed configuration and for enabling said portions of said collapsible shield means to be disposed in a generally serial relationship when said collapsible shield means is in an expanded configuration.

54. The adjustable catheter contamination shield according to claim 53 wherein at least one of said plurality of folds is disposed adjacent ends of the collapsible shield means portions.

55. The adjustable catheter contamination shield according to claim 54 wherein each of said collapsible shield means portions have approximately equal length.

56. The adjustable catheter contamination shield according to claim 55 wherein the collapsible shield means portions are generally tubular and smooth between the folds adjacent each end thereof.

57. An adjustable catheter contamination shield comprising:
- a distal fitting including bushing means for coupling to an introducer and means, defining a bore through the distal fitting, for enabling passage of a catheter therethrough;
- a proximal fitting including means, defining a bore therethrough, for enabling passage of the catheter through the proximal fitting; and
- collapsible shield means, disposed between said distal and proximal fittings, for enclosing an adjustable space therebetween and for preventing contact with a portion of the catheter disposed between the distal and proximal fittings, said collapsible shield means including means, defining a convoluted structure in which portions of the collapsible shield means overlay one another longitudinally, for controlling the expansion of the collapsible shield means as the proximal and distal fittings are moved apart from one another.

58. A procedure for providing a contamination free environment exterior to a body for a catheter comprising the steps of:
- coupling a distal fitting of a contamination shield to an introducer, the introducer being adapted for insertion into a venous vessel;
- passing the catheter through a proximal fitting and into a contamination free area enclosed by an expandable shield disposed between said distal and proximal fittings;
- expanding the shield from one end of a collapsed configuration thereof to enable visual observation of a catheter portion passing between the distal and proximal fittings.

59. The procedure according to claim 56 further including the step of manipulating the catheter while it is within the expandable shield and between the proximal and distal fittings, the manipulation including bending of the catheter within the proximal and/or distal fitting up to angles of approximately 90° without kinking of the catheter.

* * * * *